(12) United States Patent
Kannan et al.

(10) Patent No.: US 7,067,674 B1
(45) Date of Patent: Jun. 27, 2006

(54) TWO-PHOTON ABSORBING CHROMOPHORES CONTAINING POLYMERIZABLE OLEFINIC GROUPS

(75) Inventors: Ramamurthi Kannan, Cincinnati, OH (US); Loon-Seng Tan, Centerville, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 221 days.

(21) Appl. No.: 10/784,310

(22) Filed: Feb. 23, 2004

Related U.S. Application Data

(60) Provisional application No. 60/484,679, filed on Jul. 3, 2003.

(51) Int. Cl.
 *C07D 277/64* (2006.01)

(52) U.S. Cl. .................................................... 548/160

(58) Field of Classification Search ................. 548/160
 See application file for complete search history.

(56) References Cited

U.S. PATENT DOCUMENTS

| | | | |
|---|---|---|---|
| 6,100,405 A | 8/2000 | Reinhardt | |
| 6,300,502 B1 | 10/2001 | Kannan | |

OTHER PUBLICATIONS

Dang et al., Polymer Preprints (American Chemical Society, Division of Polymer Chemistry), Apr. 2002, 43(1), pp. 102-103.*

* cited by examiner

*Primary Examiner*—Laura L. Stockton
(74) *Attorney, Agent, or Firm*—AFMCLO/JAZ; Bart S. Hersko

(57) ABSTRACT

Provided are chromophores of the formula:

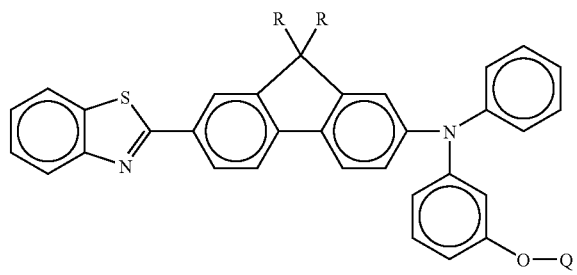

wherein R is an alkyl group having 1 to 20 carbon atoms, and Q is —$(CH_2)_n$—Br,

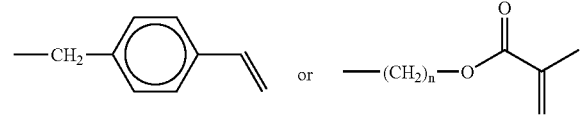

and wherein n has a value of 2–6.

6 Claims, No Drawings

TWO-PHOTON ABSORBING CHROMOPHORES CONTAINING POLYMERIZABLE OLEFINIC GROUPS

CROSS REFERENCE TO RELATED APPLICATION

This application claims priority of the filing date of Provisional Application Ser. No. 60/484,679, filed Jul. 3, 2003.

RIGHTS OF THE GOVERNMENT

The invention described herein may be manufactured and used by or for the Government of the United States for all governmental purposes without the payment of any royalty.

BACKGROUND OF THE INVENTION

The present invention relates to chromophores with very large two-photon absorption cross-sections.

Two-photon or multiphoton absorption occurs through the simultaneous absorption of two or more photons via virtual states in an absorbing medium, with the former being more common. For a given chromophore, these absorption processes take place at wavelengths much longer than the cut-off wavelength of its linear (single-photon) absorption. In the case of two-photon absorption (TPA), two quanta of photons may be absorbed from a single light source (degenerate TPA) or two sources of different wavelengths (non-degenerate TPA). Although multiphoton absorption processes have been known since 1931, this field remained dormant largely due to the lack of TPA-active materials with sufficiently large cross-sections. In the mid-1990s, several new classes of chromophores exhibiting very large effective TPA cross-section ($\sigma_2'$) values were reported. In conjunction with the increased availability of ultrafast high-intensity lasers, the renewed interest has not only sparked a flurry of activities in the preparation of novel dye molecules with enhanced $\sigma_2'$ values, but also many previously conceived applications based on TPA process in photonics and biophotonics are now enabled by these new chromophores. It is important to recognize the following features of two-photon materials technology: (a) upconverted emission, whereby an incident light at lower frequency (energy) can be converted to an output light at higher frequency, for instance, IR to UV-Vis upconversion; (b) deeper penetration of incident light; (c) highly localized excitation allowing precision control of in-situ photochemical events in the absorbing medium, thereby minimizing undesirable activities such as photodegradation or photobleaching; (d) fluorescence when properly manipulated allows information feedback. It is anticipated that further ingenious utilization of these basic characteristics will lead to practical applications other than those already emerged in such diverse areas as fluorescence imaging, data storage, eye and sensor protection, microfabrication of microelectromechanical systems (MEMS), photodynamic therapy, etc.

Accordingly, it is an object of the present invention to provide new TPA chromophores.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there are provided new TPA chromophores of the formula:

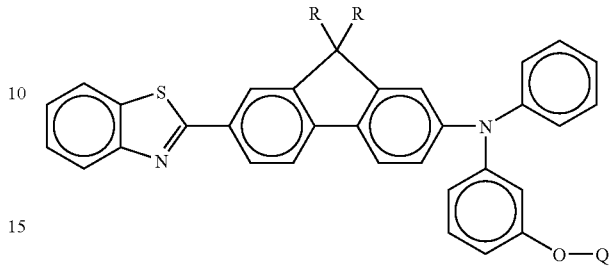

wherein R is an alkyl group having 1 to 20 carbon atoms, and Q is —$(CH_2)_n$—Br,

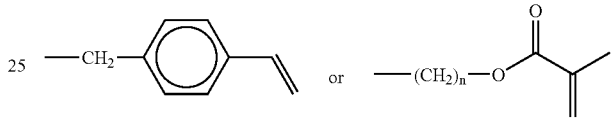

and wherein n has a value of 2–6.

The chromophores of this invention can be synthesized following the procedures given in the following Examples which illustrate the invention:

EXAMPLE 1

2,7-Dibromofluorene

To a mechanically stirred mixture of fluorene (113.76 g., 0.68 mol.), iodine (1.96 g., 0.0077 mol.), and methylene chloride (750 ml), bromine (74 ml, 1.44 mol.) diluted with methylene chloride (100 ml) was added dropwise at room temperature over a period of 1.5 hours. After 5 minutes, a solution of sodium bisulfite (15.0 g.) in water (100 ml) was added and the mixture was stirred for 30 minutes, when the mixture became colorless. Water (750 ml) was then added, and methylene chloride was distilled off. The product slurry was filtered and the product was air-dried, 220.5 g., m.p. 156–160° C. This material was used in the next step without further purification.

EXAMPLE 2

9,9-Diethyl-2,7-dibromofluorene

To a mechanically stirred mixture of 2,7-dibromofluorene (66.5 g., 0.205 mol.), powdered potassium hydroxide (56.0 g., 1.0 mol.), potassium iodide (3.4 g.) and DMSO (150 ml), cooled to 10° C., ethyl bromide (40 ml, 58.4 g. 0.536 mol.) was added dropwise over 45 minutes. The mixture turned from red to light purple. After allowing the temperature to warm to 20° C., the mixture was left overnight to stir and poured into water, 77.0 g. (98.7% yield), m.p. 144–153° C. The product was then recrystallized from hexane (550 ml) with charcoal treatment, and collected in two crops, m.p. 154–157° C. and 153–154° C., totaling 60.36 g. (77.4% yield).

EXAMPLE 3

9,9-Diethyl-7-bromo-fluorene-2-carboxaldehyde

To a mechanically stirred solution of 9,9-diethyl-2,7-dibromofluorene (59.38 g., 0.1563 mol.), in THF (325 ml), cooled in dry ice-ethanol bath, n-butyl lithium (104 ml of 1.6M solution in hexanes, 0.1664 mol, 1.06 eq.) was added dropwise over 25 minutes. After 20 minutes, DMF (17 ml, 0.22 mol.) in THF (30 ml) was added, and the mixture was stirred in the cooling bath for 1.5 hours, and outside the bath for 1 hour. The reaction was then cooled to 5° C., and treated with hydrochloric acid (12.5 ml of concentrated hydrochloric acid diluted with 50 ml water). The mixture was diluted with 200 ml of toluene, and the aqueous phase was separated and extracted with 200 ml of toluene. The combined organic phase was washed with dilute sodium bicarbonate solution, dried over magnesium sulfate and concentrated. The residual solids were recrystallized from heptane-ethyl acetate (9:1), to get colorless solids, 40.29 g. (78.4% yield) m.p. 126–128° C. The mother liquor after chromatography over 150 g. silica gel, elution with 1:1 heptane-toluene, and trituration of residual solids in hexanes gave additional product, 6.56 g. (12.8% yield, 91% total yield), m.p. 126–128° C. Mass Spec: m/z 328, 330, (M+). A sample for analysis was prepared by recrystallization from hexanes, m.p. 127–129° C. Analysis: Calculated for $C_{18}H_{17}BrO$: C, 65.55; H, 5.20; Br, 24.27%. Found: C, 65.60; H, 5.51; Br, 24.71%.

EXAMPLE 4

2-(7-Bromo-9,9-diethylfluoren-2-yl)benzothiazole

A mixture of 9,9-diethyl-7-bromo-fluorene-2-carboxaldehyde (49.35 g., 0.15 mol.), 2-amino-thiophenol (20 ml. 0.187 mol., 1,25 eq.), and DMSO (110 ml) was heated in an oil bath to a bath temperature of 195° C., held there for 45 minutes, and then poured into water. The separated solids were collected, reslurried in 1:4 acetic acid-water (1000 ml.) filtered, and washed with water and dilute sodium bicarbonate solution. These solids, 80.05 g., were then reslurried in hot ethanol, (600 ml), cooled and filtered to get the benzothiazole product, 45.69 g., m.p. 133.6–135° C. An additional 6.6 g., m.p. 134.6–135.5° C., was obtained by chromatography of the ethanol filtrate. Total recovery was 52.29 g. (80.3% yield). Mass Spec: m/z 433, 435, (M+). Calculated for $C_{24}H_{20}BrNS$: C, 66.37; H, 4.64; Br, 18.40; N, 3.23; S, 7.37%. Found: C, 66.46; H, 4.52; Br, 18.54; N, 3.14; S, 7.19%.

EXAMPLE 5

3-Benzyloxydiphenylamine

A solution containing 3-hydroxydiphenylamine (18.51 g, 0.10 mol) and potassium carbonate (27.63 g, 0.2 mol) in dimethylformamide (100 mL) was cooled to 10° C. under a nitrogen atmosphere. A solution of benzyl bromide (13 mL, 0.11 mol) was added dropwise over 30 min and the solution stirred overnight (20 h). The reaction mixture was poured into water (250 mL) resulting in a brown precipitate. The mixture was diluted with toluene (200 mL) and the organic layer was separated, washed with water and dried over $MgSO_4$. The crude product (27 g) was chromatographed on silica using a heptane: toluene (3:1; 2:1; 1:1) solution as eluent to afford the product (24.22 g, 88%) as white crystals: m.p. 51–54° C. IR (KBr; cm$^{-1}$): 3026 (Ar—C—H), 2921 and 2850 (C—H), 1594 and 1493 (Ar—C=C). $^1$H NMR (δ in ppm): 1.01 (s, 2H, N—H), 5.03 (s, 2H, $OCH_2$—Ar), 6.55–7.60 (m, 14H, Ar—H). $^{13}$CNMR (δ in ppm): 70.06, 104.45, 107.69, 110.78, 118.72, 121.78, 127.02, 127.65, 128.04. 128.69, 129.49, 130.26, 131.60, 137.10, 142.52, 144.38, 159.92. MS (m/z): 275 (M+). Anal. Calcd for $C_{18}H_{17}NO$: C, 82.86; H, 6.23; N, 5.09. Found: C, 82.76; H, 6.22; N, 5.03.

EXAMPLE 6

3-(4-Vinylbenzyloxy)diphenylamine

A mixture of 3-hydroxydiphenylamine (7.89 g, 0.043 mol) and N,N-dimethylformamide (50 mL) was cooled to 0° C. using an ice bath. Potassium carbonate (11.89 g, 0.086 mol) was added followed by the dropwise addition of 4-vinylbenzyl chloride (6.00 mL, 0.043 mol) under a nitrogen atmosphere. The reaction mixture was stirred overnight. The mixture was poured into water (600 mL), mechanically stirred for 30 min and then extracted with toluene. The toluene was dried with magnesium sulfate, filtered, and rotary-evaporated to afford a brown oil. The crude product was chromatographed on silica using toluene as an eluent and recrystallized in hexanes (100 mL) to afford the title product (9.22 g, 72%) as a brown crystal: m.p. 68–70° C.; IR (KBr) cm$^{-1}$ 3389 (N—H); 3032 (Ar—C—H); 2858 (C—H), 1593 and 1490 (Ar—C=C), 1274 (C—N), 1156 (C—O); $^1$H NMR (CDCl$_3$) δ 5.08s, 2H, CH2), 5.32 (d, 1H, CH), 5.73 (s, 1H, N—H), 5.83 (d, 2H, CH$_2$); 6.65–6.70(m, 1H, CH), 6.69–7.51(m, 13H, Ar—H); $^{13}$C NMR (CDCl$_3$) ppm 70.12, 104.51, 107.60, 110.88, 114.54, 118.80, 121.72, 126.88, 128.12, 129.81, 130.58, 136.92, 137.07, 137.73, 143.14, 145.03, 160.24; mass spectrum, m/z (relative intensity) 301 (M+, 19.53), 117 (100), 91 (8.30). Anal. Calcd for $C_{21}H_{19}NO$: C, 83.68; H, 6.35; N, 4.65; O, 5.30. Found: C, 83.69; H, 6.43; N, 4.52; O, 5.37.

EXAMPLE 7

N-Phenyl-N-(3-benzyloxyphenyl)-7-(benzothiazol-2-yl)-9,9-diethyl-fluoren-2-ylamine A mixture of 2-(7-bromo-9,9-diethylfluoren-2-yl)benzothiazole (16.5 g, 0.038 mol), 3-benzyloxydiphenylamine (12.5 g, 0.045 mol) and toluene 300 mL was refluxed for 45 min. The reaction mixture was cooled to room temperature and bis(dibenzylideneactone)palladium (0.4329 g), diphenylphosphinoferrocene (0.4072 g, 7.35×10$^{-4}$ mol) and sodium t-butoxide (5.37 g, 0.56 mol) were added to the solution. The reaction was heated at 85° C. overnight. A saturated solution of HCl/H$_2$O (100 mL) was added and the solution was extracted with toluene (200 mL). The toluene layer was dried with magnesium sulfate and rotary-evaporated to dryness. The crude product was chromatographed on silica using 1:1 toluene/hexanes followed by toluene as eluent and recrystallized from toluene/heptane (100 mL) to afford the product (92%, 21.81 g) as yellow crystals: m.p. 181–183° C. IR (KBr) cm$^{-1}$ 3060 and 3051 (Ar—C—H), 2962 and 2918 (C—H), 1592 and 1488 (Ar—C=C). $^1$H NMR (δ in ppm; CDCl$_3$) 0.43 (t, 6H, CH$_3$), 1.96–2.15 (m, 4H, CH$_2$), 4.99 (s, 2H, CH$_2$), 6.68–8.13 (m, 24H, Ar—C—H). $^{13}$C NMR ppm (δ in ppm; CDCl$_3$) 9.08, 33.09, 56.88, 70.37, 109.57, 110.82, 116.92, 119.54, 119.84, 121.48, 121.88, 121.99, 123.38, 123.47, 124.05, 124.91, 125.41, 126.72, 127.73, 127.97, 128.38, 129.00, 129.72, 130.30, 131.96, 135.37, 135.95, 137.26, 144.92, 148.08, 149.39, 149.54, 151.15, 152.50, 154.69, 160.10, 169.28. Mass spectrum, m/z (relative intensity): 628 (M$^+$, 100), 537 (10.11), 493 (27.00). Anal. Calcd for $C_{43}H_{36}N_2OS$: C, 82.13; H, 5.77; N, 4.45; S, 5.11. Found: C, 82.33; H, 5.99; N, 4.29; S, 4.99.

EXAMPLE 8

N-phenyl-N-(3-hydroxyphenyl)-7-(benzothiazol-2-yl)-9,9-diethylfluoren-2-ylamine

A mixture of N-phenyl-N-(3-benzyloxyphenyl)-7-(benzothiazol-2-yl)-9,9-diethylfluoren-2-ylamine (19.70 g, 0.03 mol) and pyridine hydrochloride (170.00 g, 1.47 mol) was heated to 200° C. for 1.5 h in an oil bath. The solution was poured into warm water (1400 mL), stirred for 20 min, filtered, and the precipitate was washed with warm water. The red precipitate was slurried in ammonium hydroxide (10%) and allowed to stir overnight, filtered, and the yellow residue was recrystallized from ethyl acetate (2550 mL, charcoal) to afford the product (14.01 g, 83%) as bright yellow crystals: m.p. 246–248° C. IR (KBr) cm$^{-1}$ 3500–3350 (OH), 3060 (Ar—C—H), 2962 and 2945 (C—H), 1596 and 1488 (Ar—C=C). $^1$H NMR: δ in ppm [DCON(CD$_3$)$_2$] 0.31 (t, 6H, CH$_3$), 1.85–2.14 (m, 4H, CH2), 6.41–8.22 (m, 19H, Ar—C—H). $^{13}$C NMR δ in ppm [DCON(CD$_3$)$_2$] 8.83, 32.81, 56.94, 111.03, 111.62, 115.33, 119.62, 120.63, 122.09, 122.26, 122.88, 123.46, 124.12, 126.05, 127.32, 127.84, 130.12, 132.15, 135.55, 135.94, 145.31, 148.47, 149.00, 149.61, 151.39, 152.65, 154.90, 159.62, 162.91, 168.77; mass spectrum, m/z (relative intensity): 538 (M$^+$, 100), 509 (33.32), 494 (8.98), 269(38.05). Anal. Calcd for $C_{36}H_{30}N_2OS$: C, 80.26; H, 5.61; N, 5.20; O, 2.97; S, 5.95. Found: C, 80.24; H, 5.69; N, 5.01; O, 3.37; S, 6.03.

EXAMPLE 9

N-phenyl-N-(3-(4-vinylbenzyloxy)phenyl)-7-(benzothiazol-2-yl)-9,9-diethyl-fluoren-2-ylamine Method (a): A mixture of N-phenyl-N-(3-hydroxyphenyl)-7-(benzothiazol-2-yl)-9,9-diethylfluoren-2-ylamine (5.00 g, 0.0093 mol) and N,N-dimethylformamide (125 mL) was cooled to 0° C. using an ice bath. Potassium hydroxide (0.99 g, 0.0176 mol) was added, followed by the dropwise addition of vinylbenzyl chloride (2 mL, 0.014 mol). Addition of the vinylbenzyl chloride caused the mixture to change from yellow in color to light brown. The reaction was stirred overnight. Potassium carbonate (2.07 g, 0.015 mol) and 3-sulfobenzoic acid (3.36 g, 0.015 mol) were added and the mixture was stirred overnight to remove any excess vinylbenzyl chloride. The mixture was poured into water (500 mL) and the product was collected by vacuum filtration. The solid was refluxed in ethanol (200 mL) for 1 h, filtered and washed with water (200 mL). The crude product was chromatographed on silica using 1:1 toluene/heptane as the eluent and recrystallized from hexanes (300 mL) to afford the product (3.39 g, 56%) as yellow crystals: m.p. 173–174° C. IR (KBr) cm$^{-1}$ 3430 (Ar—C—H), 2960 and 2922 (C—H), 1593 and 1487 (Ar—C=C), 1275 (C—N), 1219 (C—O). $^1$H NMR (δ in ppm; CDCl$_3$) 0.39 (t, 6H, CH$_3$), 1.94–2.13 (m, 4H, CH$_2$), 4.95 (s, 2H, CH$_2$), 5.26 (d, 1H, CH), 5.76 (d, 1H, CH), 6.65–6.77 (m, 1H, CH), 7.02–8.14 (m, 23H, Ar—H). $^{13}$C NMR (δ in ppm CDCl$_3$) 9.03, 33.08, 56.88, 70.12, 109.69, 110.85, 114.54, 116.93, 119.52, 119.58, 119.86, 121.53, 121.86, 121.98, 123.48, 124.04, 124.91, 126.76, 126.83, 126.87, 127.76, 128.11, 129.74, 130.33, 131.99, 135.39, 135.96, 136.85, 136.95, 137.72, 144.93, 148.08, 148.39, 149.55, 151.17, 152.51, 160.04, 169.28. Mass spectrum, m/z (relative intensity) 654 (M$^+$, 60.97), 537 (11.44), 493 (19.33). Anal. Calcd for $C_{45}H_{38}N_2OS$: C, 82.53; H, 5.85; O, 2.44; N, 4.28; S, 4.90. Found: C, 82.48; H, 5.99; O, 2.37; N, 4.12; S, 4.93.

Method (b): A mixture of 2-(7-bromo-9,9-diethylfluoren-2-yl)benzothiazole (example 4; 2.18 g, 0.005 mol) and toluene (50 mL) was heated to reflux for 45 min. The reaction was cooled to room temperature and 3-(4-vinylbenzyloxy)diphenylamine (example 6; 1.81 g, 0.006 mol), bis(dibenzylideneactone)palladium (0.0572 g, 9.95×10$^{-5}$ mol), diphenylphosphinoferrocene (0.0536 g, 9.67×10$^{-5}$ mol), and sodium t-butoxide (0.721 g, 0.0075 mol) were added to the solution and the reaction was heated at 70° C. overnight. The red solution was poured into water (250 mL) and extracted with toluene (200 mL). The toluene layer was dried with magnesium sulfate and rotary-evaporated to dryness. The crude product was chromatographed on silica using 1:1 toluene/hexanes followed by toluene as eluent and recrystallized from hexanes (300 mL) to afford 63 (1.82 g, 55%) as yellow crystals: m.p. 173–174° C.; IR (KBr) cm$^{-1}$3432 (Ar—C—H), 2959 and 2922 (C—H), 1595 and 1459 (Ar—C=C), 1276 (C—N), 1193 (C—O). $^1$H NMR (CDCl$_3$) 0.41 (t, 6H, CH$_3$), 1.94–2.17 (m, 4H, CH$_2$), 4.96 (s, 2H, CH$_2$), 5.26 (d, 1H, CH), 5.76 (d, 1H, CH), 6.64–6.81 (m, 1H, CH), 7.02–8.13 (m, 23H, Ar—H). $^{13}$C NMR (δ in ppm; CDCl$_3$) 9.07, 33.08, 56.87, 70.10, 109.65, 110.80, 114.52, 116.91, 119.53, 119.85, 121.47, 121.87, 121.98, 123.38, 123.45, 124.04, 124.88, 125.40, 126.71, 126.82, 127.71, 128.10, 129.70, 130.30, 131.95, 135.36, 135.94, 136.80, 136.87, 137.70, 144.91, 148.07, 148.36, 149.53, 151.14, 152.48, 154.69, 160.00, 169.29; mass spectrum, m/z (relative intensity) 654 (M$^+$, 67.58), 537 (100), 493 (16.03). Anal. Calcd for $C_{45}H_{38}N_2OS$: C, 82.53; H, 5.85; O, 2.44; N, 4.28; S, 4.90. Found: C, 82.12; H, 5.98; O, 2.40; N, 4.16; S, 4.82.

EXAMPLE 10

N-phenyl-N-(3-(2-bromoethoxy)phenyl)-7-(benzothiazol-2-yl)-9,9-diethyl-fluoren-2-ylamine A solution of N-phenyl-N-(3-hydroxyphenyl)-7-(benzothiazol-2-yl)-9,9-diethylfluoren-2-ylamine (5.00 g, 0.0093 mol), potassium hydroxide (2.68 g, 0.048 mol), and toluene (250 mL) was refluxed, distilled (to remove water/toluene) under a nitrogen atmosphere and cooled to room temperature using a water bath. After the addition of 1,2-dibromoethane (8.48 mL, 0.098 mol) and 18-crown-6 (0.11 g, 4.22×10$^{-4}$ mol), the mixture was refluxed for 3 h. The mixture was poured into water (400 mL) and the resulting oil was extracted with toluene (300 mL). The toluene was washed with 5% NaOH (300 mL), H$_2$O (1000 mL), dried with magnesium sulfate and rotary-evaporated to dryness to afford a yellow oil. The crude product was chromatographed on silica using 90% toluene/10% heptane as the eluent and recrystallized from hexanes (250 mL) to afford the product (3.95 g, 66%) as a yellow powder: m.p. 136–139° C.; IR (KBr) cm$^{-1}$ 3028 (Ar—C—H), 2959 and 2924 (C—H), 1588 and 1487 (Ar—C=C), 1276 (C—N), 1196 (C—O). $^1$H NMR (δ in ppm; CDCl$_3$) 0.40 (t, 6H, CH$_3$), 1.80–2.18 (m, 4H, CH$_2$), 3.80 (t, 2H, CH$_2$), 4.20 (t, 2H, CH$_2$), 6.65–8.15 (m, 19H, Ar—H). $^{13}$C NMR (δ in ppm; CDCl$_3$) 9.10, 29.58, 33.08, 56.89, 68.22, 109.25, 110.63, 117.34, 119.56, 119.88, 121.51, 121.87, 122.00, 123.38, 123.63, 124.06, 124.99, 125.42, 126.73, 127.74, 129.76, 130.42, 132.01, 135.37, 136.06, 144.86, 148.03, 148.30, 149.68, 151.15, 152.55, 154.69, 159.43, 169.25. Mass spectrum, m/z 646, 644 (M$^+$, 100, 92.45). Anal. Calcd for $C_{38}H_{33}BrN_2OS$: C, 70.69; H, 5.15; N, 4.34; O, 2.48; S, 4.97; Br, 12.37. Found: C, 70.74; H, 5.38; N, 4.19; O, 2.87; S, 5.01; Br, 12.49.

EXAMPLE 11

N-3-(4-Bromobutyloxy)-phenyl-N-phenyl-7-(benzothiazol-2yl)-9,9-diethylfluoren-2-amine A mixture of N-3-hydroxyphenyl-N-phenyl-7-(benzothiazol-2-yl)-9,9-diethylfluoren-2-amine (Example 8, 11.0 g, 20 mmol.), potassium carbonate (6.0 g, 43 mmol.), N,N-dimethylacetamide (46 ml) and toluene, was heated to reflux under nitrogen, and the toluene was distilled off. The mixture was cooled in an ice-bath, and 1,4-dibromobutane (12 ml, 100 mmol.) was added. The mixture was allowed to come to room temperature, stirred for 48 hours, and then diluted with water and toluene. The toluene phase was separated, washed successively with water and saturated sodium chloride solution, dried and concentrated. The residual oil (14 g) was chromatographed over silica gel, and the product was eluted with 3:1 toluene-heptane. The yellow glassy product on standing in isopropanol solidified, 9.64 g, (72% yield), m.p. 120.9–123.0° C. EIMS: m/z 672,674 (M$^+$). $^1$H NMR (δ in ppm; CDCl$_3$): 0.24–0.54 (t, 6H), 1.75–2.22 (m, 8H), 3.26–3.61 (m, 2H), 3.85–3.89(t, 2H), 6.54–6.86(m, 3 ArH), 6.90–8.23 (m, 16 ArH). $^{13}$C NMR (δ in ppm: CDCl$_3$): 8.61, 27.79, 29.37, 32.60, 33.41, 56.36, 66.64(sp$^3$C), 108.77, 109.95, 116.37, 118.96, 119.36, 120.98, 121.38, 121.50, 122.88, 123.00, 123.48, 124.43, 124.92, 126.22, 127.25, 129.24, 129.82, 131.46, 134.86, 135.43, 144.42, 147.61, 147.90, 149.06, 150.64, 151.99, 154.18, 159.71, 168.76 (sp$^2$C). Anal. Calcd for $C_{40}H_{37}BrN_2OS$: C, 71.31%; H, 5.53%; N, 4.15%; S, 4.76%; Br, 11.86%. Found: C, 71.32%, H, 5.65%, N, 4.05%, S, 4.82%, Br, 11.79%.

EXAMPLE 12

N-3-(6-Bromohexyloxy)-phenyl-N-Phenyl-7-(benzothiazol-2-yl)-9,9-diethylfluoren-2-yl amine Under nitrogen, from a mixture of N-3-hydroxylphenyl-N-phenyl-7-(benzothiazol-2-yl)-9,9-diethylfluorne-2-amine (Example 8; 5.56 g, 10.32 mmol.), potassium carbonate (3.0 g, 21.7 mmol.), N,N-dimethylacetamide (21 ml) and toluene (25 ml), toluene (23 ml) was distilled off, and the mixture was cooled to room temperature. 1,6-Dibromohexane (8 ml, 51.8 mmol.), was then added, and the mixture was stirred at room temperature for 72 hours. After dilution with water, the mixture was extracted with toluene, and the toluene extract was washed with water and saturated sodium chloride solution, dried and concentrated. The residual oil was chromatographed over silica gel. Elution with toluene-heptane (1:1) gave the product as a thick, yellow semi-solid, 6.29 g. On standing over methanol, the product separated as greenish yellow crystals, 6.16 g, (88% yield), m.p. 100.7–103.1° C. EIMS: m/z 700,702 (M$^+$). $^1$H NMR (δ in ppm; CDCl$_3$): 0.36–0.41 (t, 6H, CH$_3$), 1.42–1.45 (t, 4H, CH$_2$), 1.69–2.11, (m, 8H, CH$_2$), 3.35–3.39 (t, 2H, Br—CH$_2$), 3.81–3.86 (t, 2H, O—CH$_2$), 6.55–6.70 (m, 3 ArH), 7.03–8.09 (m, 16 ArH). $^{13}$C NMR (δ in ppm; CDCl$_3$): 8.61, 25.26, 27.88, 29.03, 32.60, 33.69, 56.39, 67.59 (sp$^3$ C), 108.94, 110.09, 116.31, 118.96, 119.36, 120.98, 121.41, 121.50, 122.96, 123.48, 124.43, 124.92, 126.25, 127.28, 129.24, 129.79, 131.49, 134.91, 135.40, 144.45, 147.70, 147.99, 149.03, 150.67, 152.02, 154.24, 159.94, 168.75 (sp$^2$C). Anal. Calcd. for $C_{42}H_{41}N_2BrS$: C, 71.88%; H, 5.89%; N, 3.99%; Br, 11.39%; S, 4.57%. Found: C, 71.95%; H, 5.85%; N, 3.89%; Br, 11.33%; S, 4.51%.

EXAMPLE 13

4-(3-[(7-benzothiazol-2-yl-9,9-diethylfluoren-2-yl) phenylamino]phenoxy) ethyl-2-methylprop-2-enoate A mixture of N-3-(2-bromoethoxy)-phenyl-7-(benzothiazol-2-yl)-9,9-diethylfluoren-2-amine (Example 11, 1.26 g, 2.0 mmol.), methacrylic acid sodium salt (1.08 g, 10 mmol.), potassium iodide (0.075 g, 0.45 mmol.) and dimethylformamide (10 ml), was stirred under nitrogen at room temperature for a week, and poured onto water. The separated yellow solids were filtered, washed with water and air-dried. These were then transferred to a column of silica gel and the column was eluted with 3:1 toluene-heptane to recover the unreacted starting material, 0.25 g, (20%), m.p. 135.5–137.5° C. Elution with toluene gave the product, which was recrystallized from hexanes, 0.75 g, (58% yield), m.p. 169.5–171° C. DSC showed only melting, and no exotherm until 250° C. Mass spectrum (m/z):650 (M$^+$). IR (KBr): 1719 cm$^{-1}$. $^1$H NMR (δ ppm in CDCl$_3$): 0.35, 0.38, 0.41 (t, 6H, methyls on the fluorene), 1.93 (s, 3H, Methyl), 1.90–2.11 (m, 4H, methylenes), 4.09–4.13 (m, 2H, OCH$_2$), 4.41–4.45 (m, 2H, OCH$_2$), 5.56,5.57 (d, 1H, olefinic), 6.11, 6.12 (d, 1H, olefinic), 6.57–6.74 (m, 2 ArH), 7.02–8.09 (m, 17 ArH). $^{13}$C NMR (δ in ppm; CDCl$_3$): 8.61, 12.29, 32.63, 56.41, 63.04, 65.86 (sp$^3$C) 108.85, 110.12, 116.69, 119.05, 119.39, 121.03, 121.44, 121.52, 122.93, 123.11, 123.57, 124.52, 124.95, 126.04, 126.27, 127.28, 129.27, 129.90, 131.52, 134.91, 135.55, 135.92, 144.42, 147.61, 147.90, 149.17, 150.67, 152.05, 154.24, 159.45, 167.25, 168.81 (sp$^2$ C). Anal. Calcd for $C_{42}H_{38}N_2SO_3$: C, 77.51%; H, 5.89%; N, 4.30%, S, 4.93%. Found: C, 77.63%, H, 5.81%, N, 4.66%, S, 4.80%.

EXAMPLE 14

4-(3-[(7-benzothiazol-2-yl-9,9-diethylfluoren-2-yl) phenylamino]phenoxy) butyl-2-methylprop-2-enoate A mixture of sodium methacrylate (2.715 g, 25.1 mmol.), N-3-(4-bromobutyloxy)phenyl-N-phenyl-7-(benzothiazol-2-yl)-9,9-diethylfluoren-2-amine (3.556 g, 5.29 mmol), Aliquat-336 (tricaprylmethyl ammonium chloride; 0.25 g, 0.62 mmol.), toluene (10 ml) and water (10 ml) was kept at 70° C. for a total of 48 hours. To the mixture, additional amounts of sodium methacrylate (1.35 g, 12.5 mmol. and 1.30 g, 12.0 mmol.), were added after 24 and 30 hours respectively. The mixture was cooled, diluted with toluene, toluene phase was washed with water, dried and concentrated to get a pale yellow viscous liquid, 4,34 g. This was transferred to a column of silica gel, and elution of the column with toluene gave the methacrylate as a yellow brittle glass, 1.78 g, (51% yield), melting range, 60.4–65° C. The DSC did not show any melting, but showed an exotherm at 137° C. Mass spectrum (m/z):678 (M$^+$). IR (KBr): 1715 cm$^{-1}$. $^1$H NMR (δ ppm in CDCl$_3$): 0.35, 0.38, 0.41 (t, 6H, methyls), 1.82–2.14 (m, 11H, methyl and methylenes), 3.88 (br t, 2H, OCH$_2$), 4.18 (br t, 2H, OCH$_2$), 5.52–5.31 (m, 1H, olefinic), 6.08 (s, 1H, olefinic), 6.55–6.71 (m, 3 ArH), 7.01–7.52 (m, 10 ArH), 7.60–7.70 (m, 2 ArH), 7.88–8.09 (m, 4 ArH). $^{13}$C NMR (δ ppm in CDCl$_3$): 8.61, 18.32, 25.37, 25.92, 32.63, 56.41, 64.28, 67.13 (sp$^3$C), 108.85, 110.00, 116.40, 118.96, 119.39, 121.00, 121.41, 121.52, 122.94, 122.99, 123.48, 124.43, 124.95, 125.35, 126.28, 127.28, 129.24, 129.85, 131.49, 134.91, 135.43, 136.35, 144.48, 147.70, 147.99, 149.05, 154.21, 159.94, 167.46, 168.78 (sp$^2$C). Anal. Calcd. for C$_{46}$H$_{46}$N$_2$O$_3$S: C, 78.15%; H, 6.55%, N, 3.93%, S, 4.53%. Found: C, 78.14%; H, 6.52%; N, 3.78%; S, 4.56%.

The TPA values of the chromophores are shown in the following table. The TPA and linear optical properties of the chromophores AF-240 and AF-341 are included for comparison:

TABLE

| Chromophore (Example No.) | λmax (nm) Linear Abs. (Upconv. Emission.) | β cm/GW at 0.2 mol/L | $\sigma'_2 (\times 10^{-48})$ $\frac{cm^4 \cdot sec}{ph \cdot molecule}$ | $\sigma'_2 /MW (\times 10^{-50})$ $\frac{cm^4 \cdot sec \cdot mole}{ph \cdot molecule \cdot g}$ |
|---|---|---|---|---|
| AF-240* | 395 (479) | 4.7 | 97.5 | 18.7 |
| AF-341 (8)** | 393 (474) | 7.5 | 155.8 | 28.9 |
| AF-343 (10) | 390 (471.6) | 4.0 | 81.0 | 12.6 |
| AF-343-21 (13) | 391, 305 (472) | 6.8 | 56.5 | 21.5 |
| AF-343-41 (14) | 391.5 (474) | — | 72.6 | 10.7 |
| AF-343-6 (12) | 394 (475) | 2.7 | 55.9 | 7.8 |
| AF-343-62 (15) | 392, 305 471.2 | 10.1 | 208 | 15.9 |
| AF-343-64 | 392 (474) | 3.2 | 65.9 | 9.32 |
| AF-344 (9) | 391.5 (472) | 3.4 | 70.0 | 10.7 |

*(7-benzothiazol-2-yl-9,9-diethylfluoren-2-yl)diphenylamine
**N-phenyl-N-(3-hydroxyphenyl)-7-(benzothiazol-2-yl)-9,9-diethylfluoren-2-ylamine 150.67, 152.02, 154.24, 159.80, 167.40, 168.81.(sp$^2$C). Anal. Calcd. for C$_{44}$H$_{42}$N$_2$O$_3$S: C, 77.84%; H, 6.23%; N, 4.12%; S, 4.72%. Found: C, 77.81%, H, 6.31%; N, 4.12%; S, 4.66%.

EXAMPLE 15

4-(3-[(7-benzothiazol-2-yl-9,9-diethylfluoren-2-yl) phenylamino]phenoxy) hexyl-2-methylprop-2-enoate A mixture of N-3-(6-bromohexyloxy)-phenyl-N-phenyl-7-(benzothiazol-2-yl)-9,9-diethylfluoren-2-amine (3.51 g, 5 mmol.), sodium methacrylate (2.71 g, 25 mmol.), benzyl tributylammonium chloride (0.161 g, 0.52 mmol.), toluene (10 ml) and water (10 ml) was kept at 70° C. for 5 days. During this period, additional amounts of sodium methacrylate (1.35 g, 12.5 mmol., and 0.62 g, (6 mmol.) were added on the third and fourth day of the reaction. The reaction was then cooled, diluted with toluene; toluene phase was washed with water, dried and concentrated to get 3.70 g of a yellow viscous liquid. This was chromatographed over silica gel and elution with toluene gave the product, 1.70 g, (48%), as a viscous liquid. Mass spectrum (m/z):706 (M$^+$). IR (KBr): 1726 cm$^{-1}$. $^1$H NMR (δ in ppm; CDCl$_3$): 0.38 (t, 6H), 1.40–1.44 (m, 4H), 1.65–1.75 (m, 4H), 1.90–2.11 (m, 4H), 3.84 (t, 2H), 4.13 (t, 2H), 5.52 (t, 1H), 6.08 (s, 1H), 6.56–6.71 (m, 3 ArH), 7.03–7.51 (m, 10 ArH), 7.59–7.70 (m, 2ArH), 7.87–8.09 (m, 4 ArH). $^{13}$C NMR (δ in ppm): 8.61, 18.32, 25.77, 28.51, 29.14, 32.60, 56.39, 64.59, 67.62 (sp$^3$C), 108.91, 110.03, 116.28, 118.90, 119.34, 120.98, 121.38, 121.50, 122.94, 123.45, 124.40, 124.92, 125.21, 126.25, 127.25, 129.21, 129.79, 131.46, 134.89, 135.38, 136.41, 144.45, 147.67, 147.99, 149.00, 150.64, 151.99,

Having thus described exemplary embodiments of the present invention, it should be noted by those skilled in the art that the disclosures herein are exemplary only and that alternatives, adaptations and modifications may be made within the scope of the present invention.

We claim:

1. A chromophore of the formula:

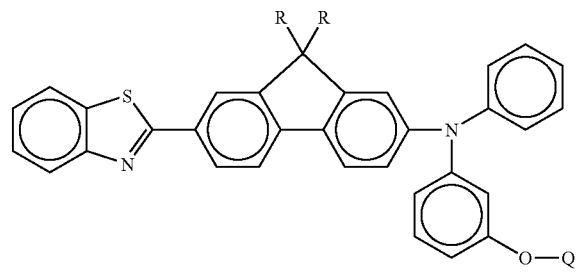

wherein each R is an alkyl group having 1 to 20 carbon atoms and Q is

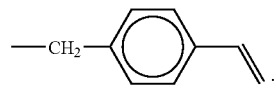

.

2. A chromophore of the formula:
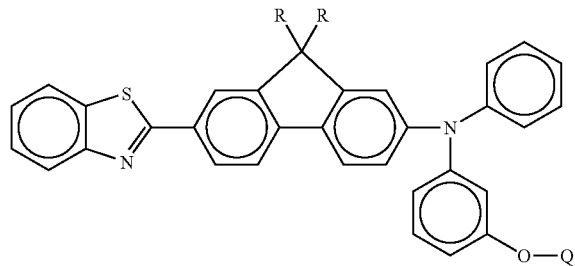
wherein each R is an alkyl group having 1 to 20 carbon atoms and Q is
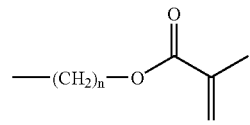
wherein n has a value of 2–6.
3. The chromophore of claim 2 wherein R is ethyl and n is 2.
4. The chromophore of claim 2 wherein R is ethyl and n is 4.
5. The chromophore of claim 2 wherein R is ethyl and n is 6.
6. The chromophore of claim 1 wherein R is ethyl.
* * * * *